(12) United States Patent
Chin et al.

(10) Patent No.: US 9,861,379 B2
(45) Date of Patent: Jan. 9, 2018

(54) TISSUE APPROXIMATOR DEVICE

(71) Applicant: Surgimatix, Inc., Oak Brook, IL (US)

(72) Inventors: Wai Ngai Chin, Glenview, IL (US); Gary M. Kobylewski, Hoffman Estates, IL (US); Adam A. Saban, Lockport, IL (US); Jafar S. Hasan, Oak Brook, IL (US)

(73) Assignee: Surgimatix, Inc., Elk Grove Village, IL (US)

( * ) Notice: Subject to any disclaimer, the term of this patent is extended or adjusted under 35 U.S.C. 154(b) by 247 days.

(21) Appl. No.: 14/739,933

(22) Filed: Jun. 15, 2015

(65) Prior Publication Data

US 2016/0015405 A1 Jan. 21, 2016

Related U.S. Application Data

(60) Provisional application No. 62/015,068, filed on Jun. 20, 2014.

(51) Int. Cl.
*A61B 17/08* (2006.01)
*A61D 1/00* (2006.01)
*A61B 17/29* (2006.01)

(52) U.S. Cl.
CPC ............. *A61B 17/29* (2013.01); *A61B 17/08* (2013.01); *A61B 2017/081* (2013.01); *A61B 2017/294* (2013.01); *A61B 2017/2911* (2013.01); *A61B 2017/2923* (2013.01); *A61B 2017/2933* (2013.01); *A61B 2017/2938* (2013.01); *A61B 2017/2944* (2013.01)

(58) Field of Classification Search
CPC ... A61B 17/08; A61B 17/29; A61B 2017/081; A61B 2017/2911; A61B 2017/2923; A61B 2017/2933; A61B 2017/2938; A61B 2017/294; A61B 2017/2944; A61B 17/0469; A61B 17/0482; A61B 17/068; A61B 2017/2927
USPC ............................. 606/139, 216; 227/175.1
See application file for complete search history.

(56) References Cited

U.S. PATENT DOCUMENTS

| | | | |
|---|---|---|---|
| 5,578,031 A | | 11/1996 | Wilk et al. |
| 5,759,193 A | * | 6/1998 | Burbank ................. A61B 17/08 606/151 |
| 6,267,761 B1 | * | 7/2001 | Ryan .................. A61B 18/1442 606/32 |
| 2007/0198038 A1 | | 8/2007 | Cohen et al. |
| 2008/0228199 A1 | | 9/2008 | Cropper et al. |
| 2009/0192529 A1 | | 7/2009 | Kaveney |
| 2012/0265218 A1 | | 10/2012 | Chen et al. |

(Continued)

OTHER PUBLICATIONS

International Search Report for related International Application No. PCT/US15/035860; report dated Oct. 2, 2015.

*Primary Examiner* — Katherine M Shi
(74) *Attorney, Agent, or Firm* — Miller, Matthias & Hull LLP

(57) ABSTRACT

An approximator device is provided. The approximator device may include an elongate member having a working end and a control end, at least two prongs disposed on the working end configured to engage tissue and longitudinally interface with one another, and a control mechanism disposed at the control end operatively coupled to one or more of the prongs and configured to longitudinally move the one or more prongs between an open position and an approximating position.

21 Claims, 15 Drawing Sheets

(56) References Cited

U.S. PATENT DOCUMENTS

2013/0317543 A1 11/2013 Rabin et al.
2014/0243890 A1* 8/2014 Dumot .................. A61B 17/08
  606/216

* cited by examiner

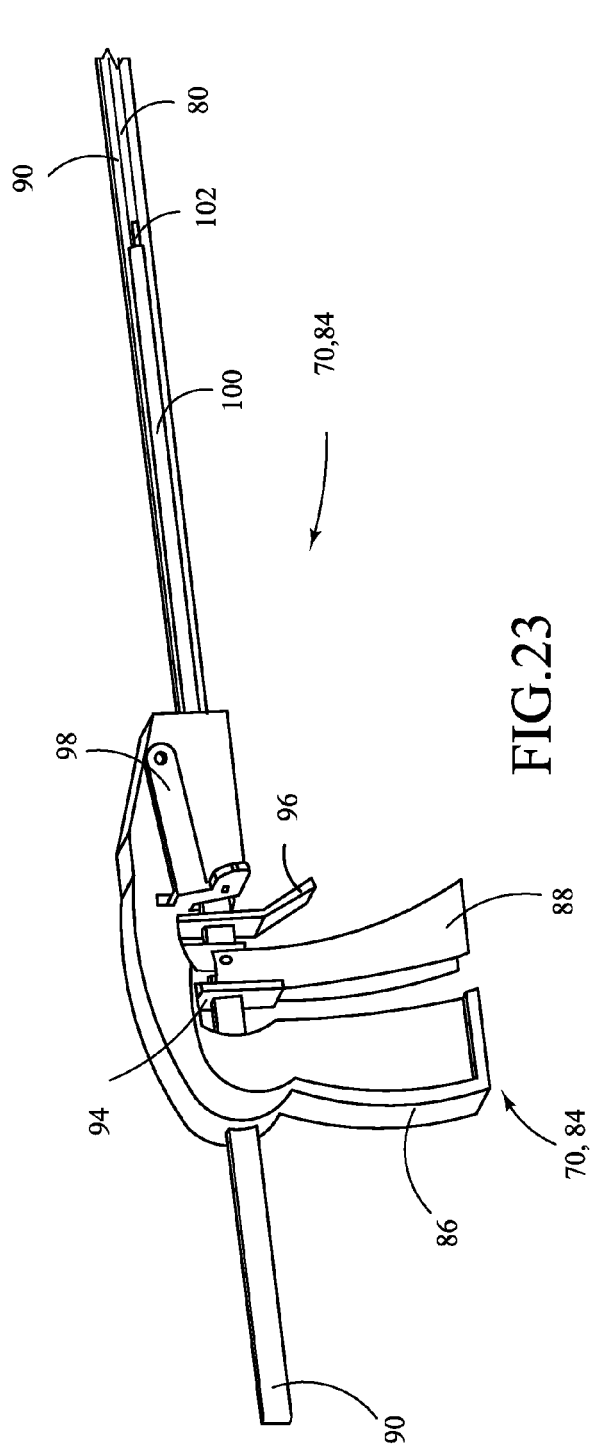
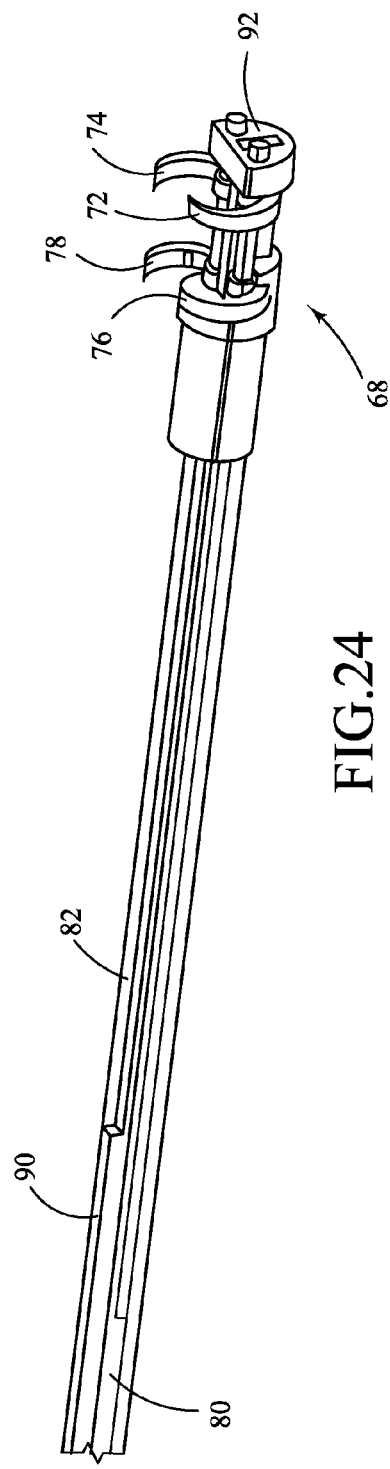
FIG.23
FIG.24

TISSUE APPROXIMATOR DEVICE

CROSS-REFERENCE TO RELATED APPLICATION

This application is based on and claims priority from U.S. Provisional Application Ser. No. 62/015,068, filed on Jun. 20, 2014.

FIELD OF THE DISCLOSURE

The present disclosure generally relates to medical devices, and more particularly, relates to tools for approximating separated tissue and facilitating tissue fixation.

BACKGROUND OF THE DISCLOSURE

Medical devices are constantly being improved upon to not only aid surgical processes, but also to help minimize the invasiveness of operations. Among other developments, much improvement has been made to medical tools, instruments, systems and procedures to enable or facilitate minimally invasive procedures. Specifically, by minimizing the incisions necessary for completing a surgical procedure, minimally invasive procedures may provide for not only shorter operation times, but also substantially shorter recovery times as well. However, making fewer and smaller incisions substantially limits access to surgical regions of interest and makes it more difficult for a surgeon to effectively complete a given task.

In a laparoscopic procedure for repairing a hernia, for instance, thin, elongated instruments or tools are inserted into relatively small incisions via access ports or trocars in the abdomen to access hernia defects in the abdominal wall from the inside. Among the tasks involved in treating a hernia defect, a surgeon may need to close and fixate separations in the tissue of the abdominal wall associated with the hernia. While laparoscopic tools and instruments for fastening tissue exist, there is no adequate device for approximating, or holding the edges of separated tissue together. Specifically, with only limited access to the interior of the abdominal wall, it is relatively difficult to approximate the edges of tissue together sufficiently to achieve more efficient tissue fixation.

Accordingly, there is a need for minimally invasive means for approximating tissue to facilitate tissue fixation, not only in association with laparoscopic procedures, but for use with any other open medical procedure involving other cavities within the body and for approximating other bodily tissues. The present disclosure serves to address this need and overcome the deficiencies set forth above. However, it should be appreciated that the solution of any particular problem is not a limitation on the scope of this disclosure or of the attached claims except to the extent express noted. Additionally, the inclusion of any problem or solution in this Background section is not an indication that the problem or solution represents known prior art except as otherwise expressly noted.

SUMMARY OF THE DISCLOSURE

In accordance with one aspect of the disclosure, an approximator device is provided. The approximator device may include an elongate member having a working end and a control end, at least two prongs disposed on the working end configured to engage tissue and longitudinally interface with one another, and a control mechanism disposed at the control end operatively coupled to one or more of the prongs and configured to longitudinally move the one or more prongs between an open position and an approximating position.

In accordance with another aspect of the disclosure, another approximator device is provided. The approximator device may include an elongate member having a working end and a control end, one or more distal prongs pivotally disposed on the working end, one or more proximal prongs pivotally disposed on the working end, and a control mechanism disposed at the control end and operatively coupled to one or more of the distal prongs and the proximal prongs. The control mechanism may be configured to cause one or more of the distal prongs and the proximal prongs to longitudinally move between an open position and an approximating position, and pivotally move between an extended position and a collapsed position.

In accordance with yet another aspect of the disclosure, an approximator device is provided. The approximator device may include an elongate member having a working end and a control end, a deployment mechanism disposed at the control end, and an approximating mechanism disposed at the control end. The working end may include a distal prong set and a proximal prong set. The deployment mechanism may be operatively coupled to each of the distal prong set and the proximal prong set, and configured to pivotally move one or more of the distal prong set and the proximal prong set between an extended position and a collapsed position. The approximating mechanism may be operatively coupled to one or more of the distal prong set and the proximal prong set, and configured to longitudinally move one or more of the distal prong set and the proximal prong set between an open position and an approximating position.

These and other aspects and features of the disclosure will be better understood upon reading the following detailed description when taken into conjunction with the accompanying drawings.

BRIEF DESCRIPTION OF THE DRAWINGS

FIG. 23 is a partial perspective view of the control end of an approximator device having ratcheting and lever-type deployment control mechanisms;

FIG. 24 is a partial perspective view of the working end of an approximator device having distal and proximal sets of prongs coupled to a tension bar and deployment shafts;

Figure 1:
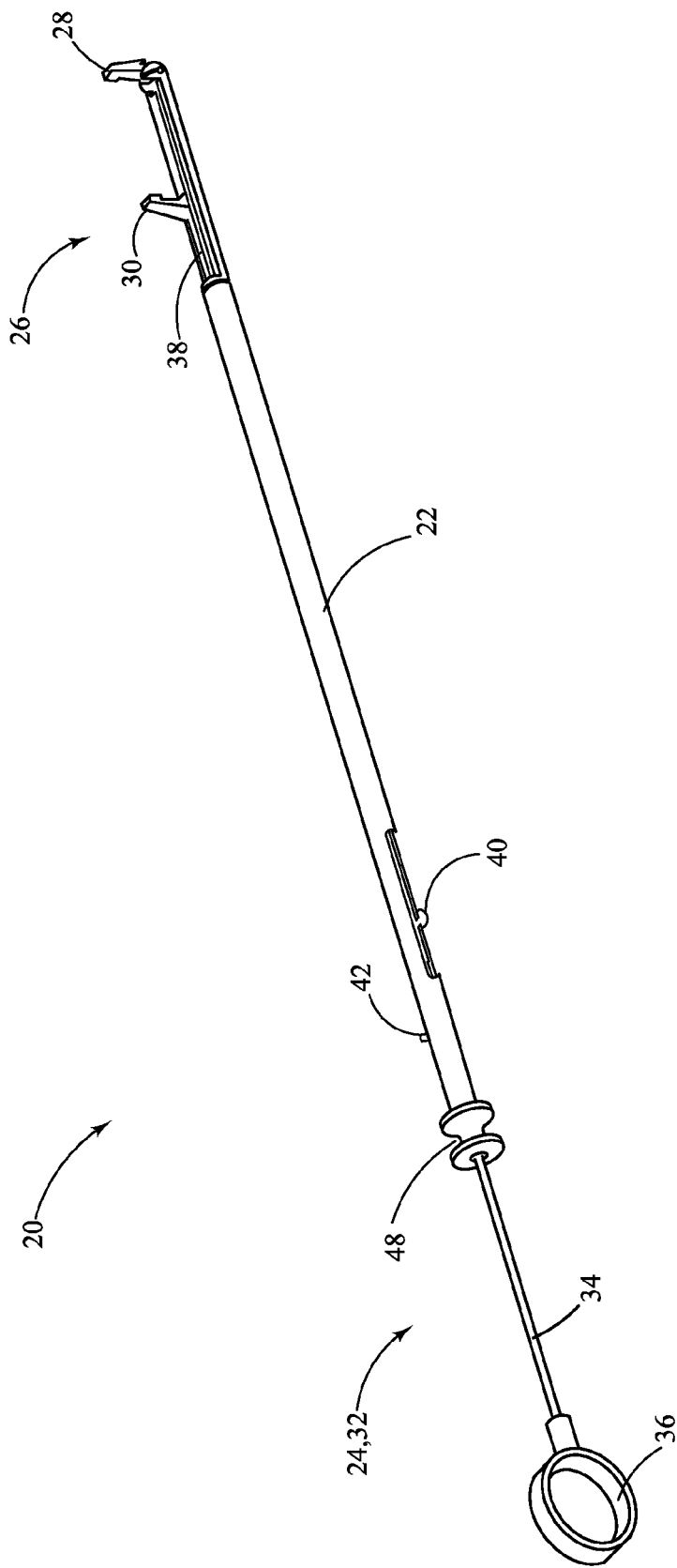
FIG. 1 is a perspective view of one approximator device constructed in accordance with the teachings of the present disclosure.

While the present disclosure is susceptible to various modifications and alternative constructions, certain illustrative embodiments thereof have been shown in the drawings and will be described below in detail. It should be understood, however, that there is no intention to limit the present invention to the specific forms disclosed, but on the contrary, the intention is to cover all modifications, alternative constructions and equivalents falling within the spirit and scope of the present disclosure.

DETAILED DESCRIPTION

Referring now to the drawings, exemplary embodiments of a tissue approximator device, constructed in accordance with the teachings of the present disclosure are shown and described. As will be described in further detail herein, the approximator device may provide a convenient and yet effective means for approximating, such as pulling and/or holding together, separated edges of tissue. The disclosed embodiments may also be used in association with minimally invasive surgical procedures, such as laparoscopic procedures, and the like. As used for laparoscopic treatment of a hernia, for example, the disclosed embodiments may be used to reach beneath sections of tissue within the abdominal wall, and approximate torn or separated edges within the tissue while fasteners are installed to close the separation in the abdominal wall from the inside. Although the embodiments disclosed herein demonstrate tissue fastening as applied to laparoscopic applications, it will be understood that the present disclosure may be equally or similarly applied to other non-laparoscopic or open medical procedures including, but not limited to, uses within the thorax, pelvis, or body cavities other than the abdomen, and uses for approximating tissues other than in the abdominal wall, such as tissues of the uterus, genitourinary system, gastrointestinal tract, musculoskeletal system, and the like.

As shown in FIG. 1, one exemplary embodiment of an approximator device 20 may include an elongate member 22 which extends between a control end 24 disposed at a proximal end thereof and a working end 26 disposed at a distal end thereof. In general, the working end 26 may include at least two prongs, such as a distal prong 28 and a proximal prong 30, which are movably disposed relative to the elongate member 22 and adapted to interface with one another to approximate, or pull and/or hold together, edges of tissue. More specifically, the prongs 28, 30 may be longitudinally movable substantially along the longitudinal axis of the elongate member 22 between an open position, as shown for example in FIG. 2, for receiving two or more edges of separated tissue, and an approximating position, as shown for example in FIG. 3, for joining edges of tissue. In the particular embodiment shown, the distal prong 28 may be held to be stationary while the proximal prong 30 is slidably movable relative thereto. In alternative embodiments, the proximal prong 30 may remain stationary while the distal prong 28 moves relative thereto. In other variations, both of the prongs 28, 30 may be movable relative to the working end 26 between the open and approximating positions.

Figure 2:
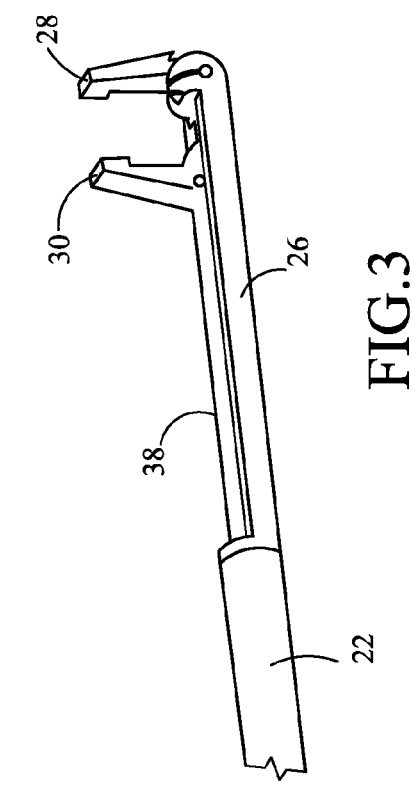
FIG. 2 is a partial perspective view of the working end of an approximator device with extended distal and proximal prongs in the open position.
Figure 3:
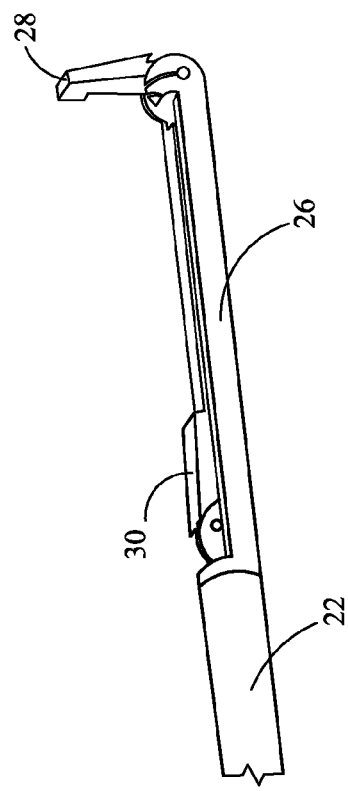
FIG. 3 is a partial perspective view of the working end of an approximator device with extended distal and proximal prongs in the approximating position.
Figure 4:
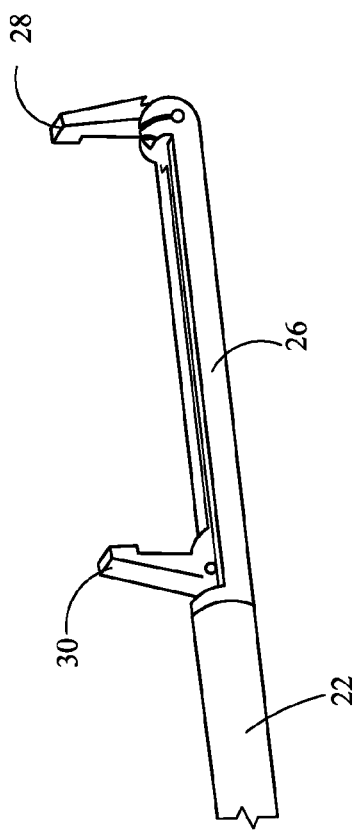
FIG. 4 is a partial perspective view of the working end of an approximator device with collapsed distal and proximal prongs in the open position.

In addition to longitudinal movements, the prongs 28, 30 of the approximator device 20 may also be pivotally movable between raised or extended positions, as shown for example in FIGS. 2-3, and fully collapsed positions, as shown for example in FIG. 4. Furthermore, the prongs 28, 30 may be sized and configured such that, when the prongs 28, 30 are fully collapsed, the maximum outer diameter of the working end 26 is less than or at most substantially equal to the maximum outer diameter of the elongate member 22 so as to facilitate entry or insertion of the working end 26 into access ports, or the like, as well as to facilitate removal therefrom. In other alternatives, the prongs 28, 30 may be sized and configured such that, when fully collapsed, the prongs 28, 30 and the working end 26 is at least partially retractable within the distal end of the elongate member 22 or a sleeve thereof. In related modifications, one or more of the prongs 28, 30 may also be biased in the extended position using springs or other means, such that the prongs 28, 30 collapse when retracted within the elongate member 22, an access port, or the like, and automatically extended once the working end 26 is advanced into the region of interest.

Figure 5:
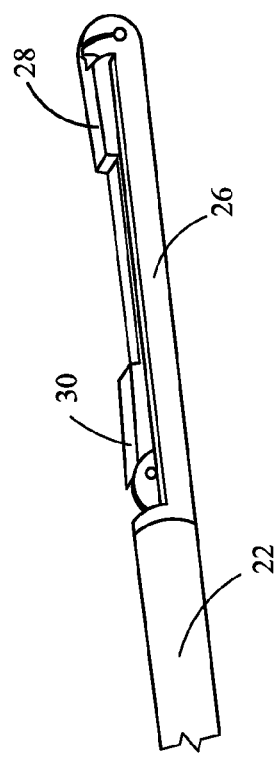
FIG. 5 is a partial perspective view of the working end of an approximator device with an extended distal prong and a collapsed proximal prong in the open position.

Still referring to FIGS. 2-4, any one or more of the prongs 28, 30 may be configured to be pivot about an axis that is substantially perpendicular to the longitudinal axis of the elongate member 22. More particularly, the prongs 28, 30 may be opposedly configured such that, when in the extended positions, the distal prong 28 may be proximally-facing and the proximal prong 30 may be distally-facing in a manner designed to facilitate approximation of tissue edges. In other embodiments, one or more of the prongs 28, 30 may be configured to pivot about an axis that is substantially parallel to the longitudinal axis of the elongate member 22. The pivotal movements of the prongs 28, 30 may also be controlled dependently or independently of the longitudinal movements. Furthermore, as shown for example in FIG. 5, each of the prongs 28, 30 may be individually controlled and movable between the collapsed and extended positions. In other modifications, the working end 26 may be provided with more than two prongs 28, 30, and in still further modifications, the prongs 28, 30 may be moved between the collapsed and extended positions, and/or moved between open and approximating positions, in manners other than the configurations shown.

The control end 24 of FIG. 1 may generally include one or more control mechanisms 32 which may employ any one or more of a variety of different means or mechanisms to operate the prongs 28, 30. In the embodiment shown, for example, the control mechanism 32 may employ a pushrod 34 with a thumb ring 36, or the like, that can be slidably pushed or pulled relative to the elongate member 22 to longitudinally move one or more of the prongs 28, 30 between the open and approximating positions shown in FIGS. 2-3. The elongate member 22 may further include a finger support 48 disposed at a proximal end thereof. In particular, the finger support 48 may be shaped or configured to not only facilitate longitudinal control of the pushrod 34 and the thumb ring 36 relative to the elongate member 22, but also to maintain such control irrespective of the rotational position of the pushrod 34 and the thumb ring 36 relative to the elongate member 22. Furthermore, as shown in more detail in FIGS. 6-8, the pushrod 34 may be coupled directly or indirectly to the proximal prong 30 via a tension bar 38 disposed within the elongate member 22 such that longitudinal movements of the pushrod 34 at the control end 24 is translated into corresponding longitudinal movements of the proximal prong 30 at the working end 26. In other embodiments, the control mechanism 32 may include threaded or screw-type means to advance or retract one or more of the prongs 28, 30 between open and approximating positions. In still further alternatives, the control end 24 may employ other means or modes to effectuate the same or similar results.

Figure 6:
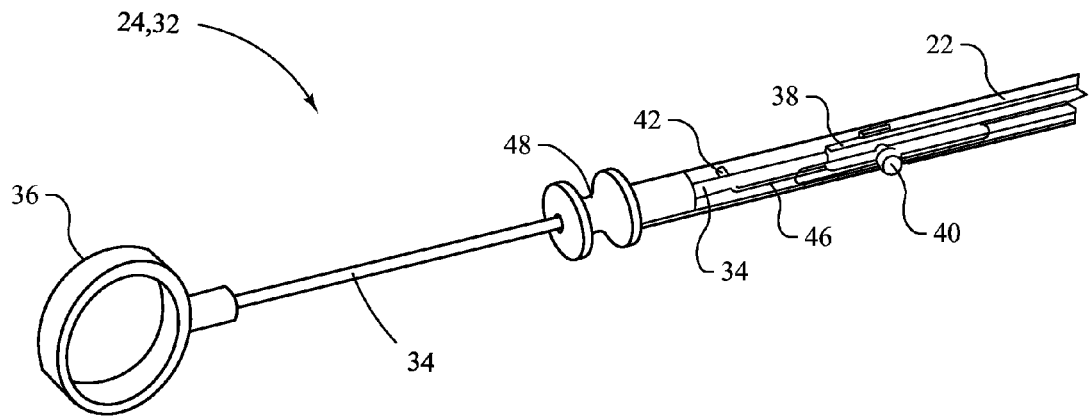
FIG. 6 is a partial perspective view of the control end of an approximator device having a pushrod control mechanism with a finger support and a deployment screw.
Figure 7:
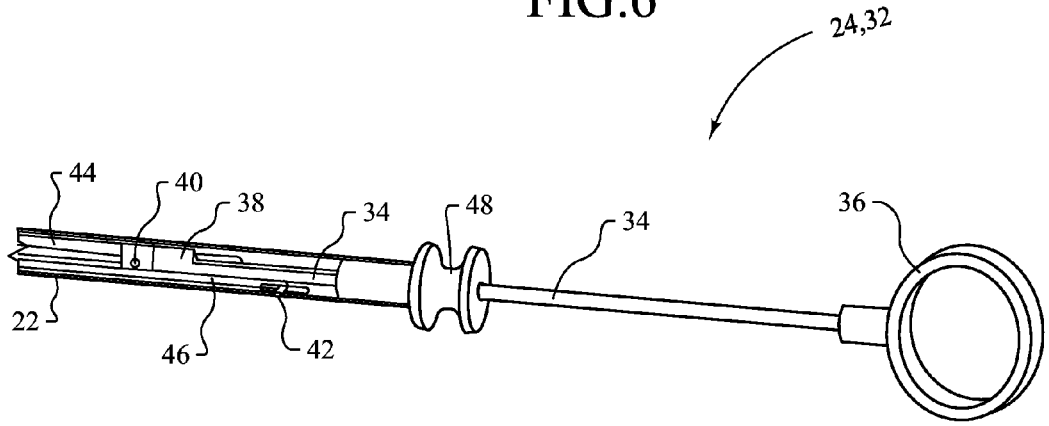
FIG. 7 is a partial perspective view of the control end of an approximator device having a pushrod control mechanism with a finger support and a deployment switch.
Figure 8:
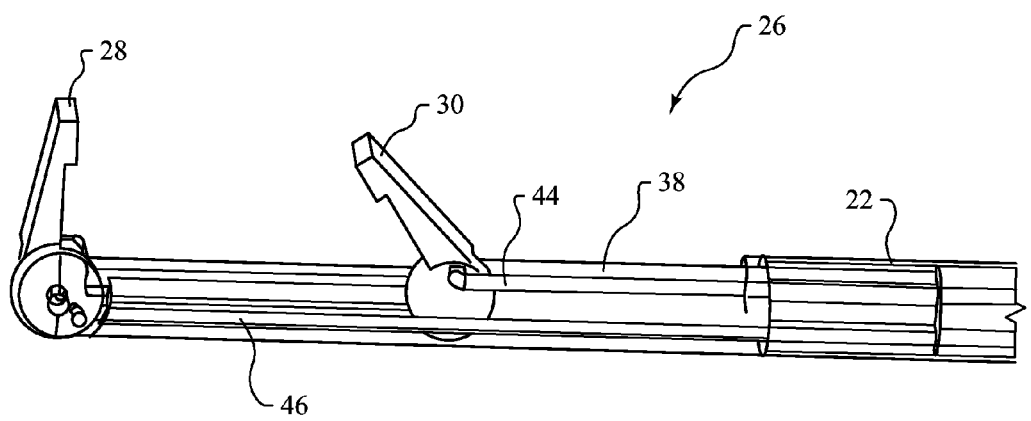
FIG. 8 is a partial perspective view of the working end of an approximator device having an extended distal prong and a partially extended proximal prong in the partially approximating position.

The control mechanism 32 may also provide one or more deployment mechanisms, such as the deployment screw 40 and the deployment switch 42 shown in FIGS. 6-8, to adjust the angular position of the prongs 28, 30 between the collapsed and extended positions. The deployment screw 40 of FIG. 6, for example, may be operatively coupled to the proximal prong 30 via the first deployment link 44 of FIG. 8 that is disposed alongside the tension bar 38 within the elongate member 22. The deployment screw 40 may also be configured to selectively couple the first deployment link 44 to the tension bar 38, so as to either enable or prevent adjustments to the angular position of the proximal prong 30 relative to the working end 26. More specifically, the deployment screw 40 may be configured such that, once loosened, the longitudinal position of the first deployment link 44 may be adjusted relative to the tension bar 38 to effectuate a corresponding adjustment in the angular position of the proximal prong 30. Alternatively, when the deployment screw 40 is sufficiently tightened, the first deployment link 44 may be locked to the tension bar 38 such that longitudinal movements in the tension bar 38 correspond to equal movements in the first deployment link 44, thereby maintaining the angular position of the proximal prong 30 when approximating.

Figure 9:
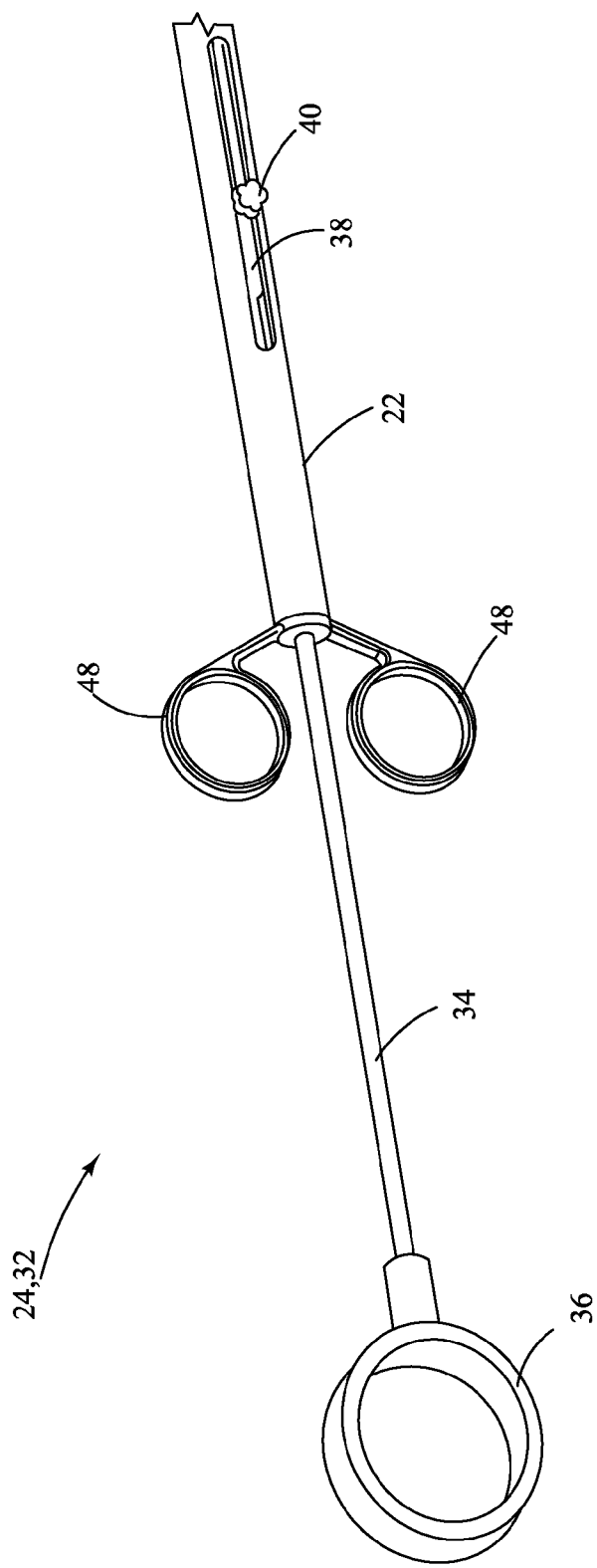
FIG. 9 is a partial perspective view of the control end of an approximator device having a pushrod control mechanism with a finger support in the form of loops.
Figure 10:
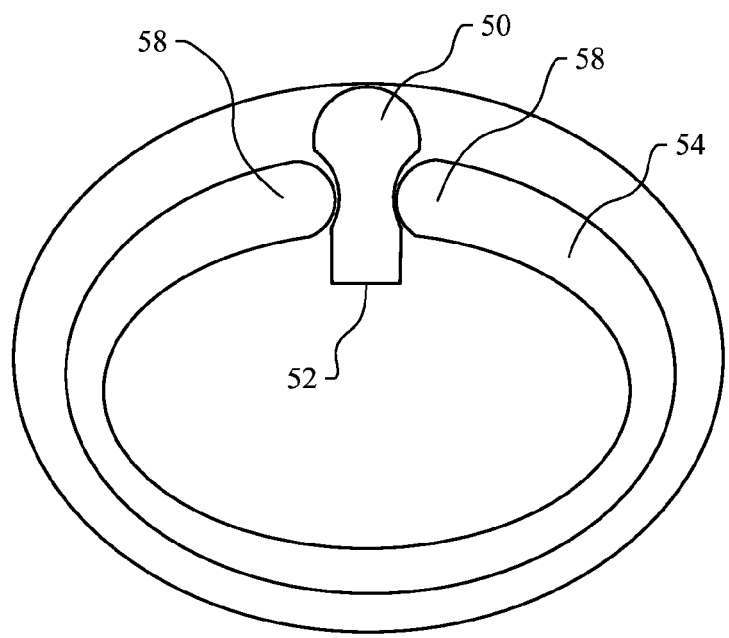
FIG. 10 is a cross-sectional diagrammatic view of a ventral hernia.
Figure 11:
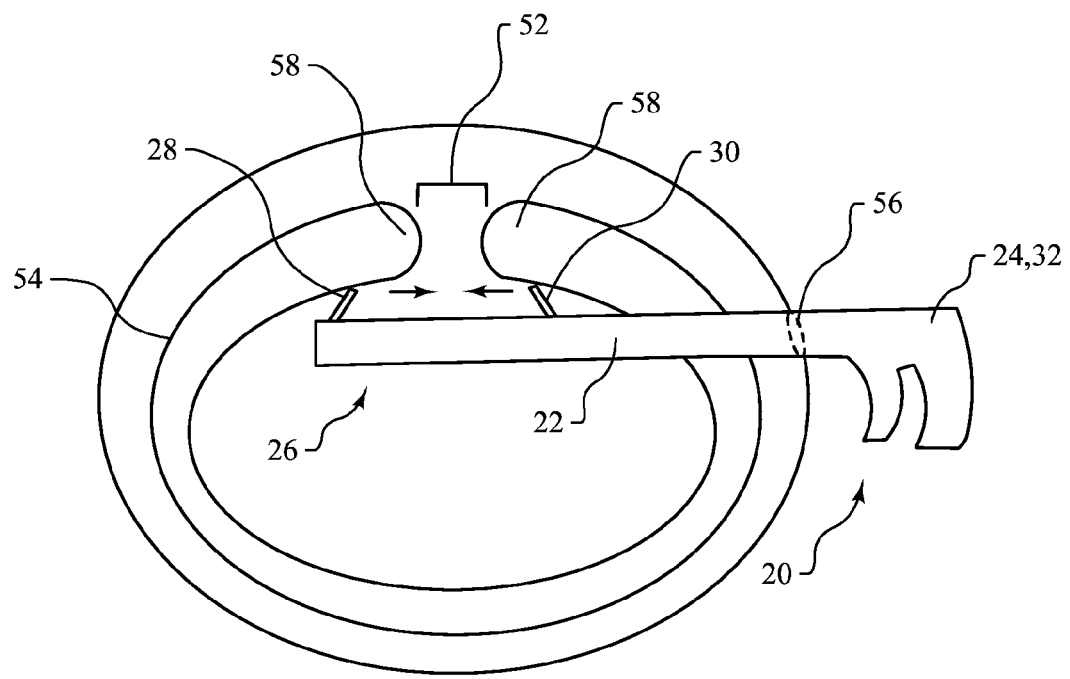
FIG. 11 is a cross-sectional diagrammatic view of abdominal tissue edges being approximated using an approximator device.

The deployment switch 42 of FIG. 7 may be similarly coupled to the distal prong 28 via the second deployment link 46 shown in FIG. 8, which may also be disposed alongside the tension bar 38 and the first deployment link 44 within the elongate member 22. Similar to the first deployment link 44, the second deployment link 46 may be coupled to the distal prong 28 in a manner which enables the distal prong 28 to be extended or collapsed based on the longitudinal position of the deployment switch 42 and the second deployment link 46 relative to the elongate member 22. Furthermore, as the distal prong 28 is not longitudinally movable in the embodiment shown, the second deployment link 46 may be operated independently from the tension bar 38. While only one particular arrangement of the control mechanism 32 is shown, other deployment and/or control mechanisms will be apparent to those of ordinary skill in the relevant art. In other modifications, for example, the first deployment link 44 and the proximal prong 30 may be operated by a deployment switch, and/or the second deployment link 46 and the distal prong 28 may be operated by a deployment screw. Additionally, as shown in FIG. 9 for example, the control end 24 of the elongate member 22 may also be provided with a finger support 48, provided in the form of one or more finger loops, or the like, to be used in conjunction with the thumb ring 36 and configured to facilitate use of the pushrod 34 during tissue approximations.

Turning now to FIGS. 10-15, one exemplary application of the approximator device 20 is shown. As shown for example in FIG. 10, the approximator device 20 may be used to aid in the repair of a ventral hernia 50 and to help close separations 52 within the tissue of the abdominal wall 54 that led to the hernia 50. In particular, once the protruding hernia contents 50 are pushed back beneath the abdominal wall 54 and prior to closing the opening 52, the working end 26 of the approximator device 20 may be inserted through an access port 56 in the abdominal wall 54, as shown in FIG.

Figure 12:
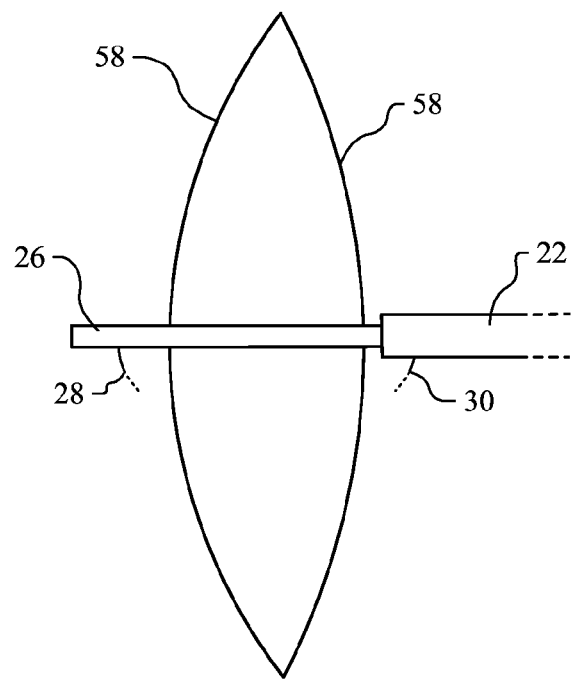
FIG. 12 is a diagrammatic view of an approximator device being positioned proximate to tissue edges.

11, in order to approximate the tissue edges 58 surrounding the opening 52. The distal and proximal prongs 28, 30 may be collapsed while inserting the working end 26 through the access port 56 and extended once placed in proximity to the separated tissue edges 58. Moreover, once fully inserted and in position, the distal and proximal prongs 28, 30 may also be longitudinally controlled into the open position as illustrated in FIG. 12, such that the distal prong 28 is in proximity to one tissue edge 58 and the proximal prong 30 is in proximity to a counterpart tissue edge 58.

Figure 13:
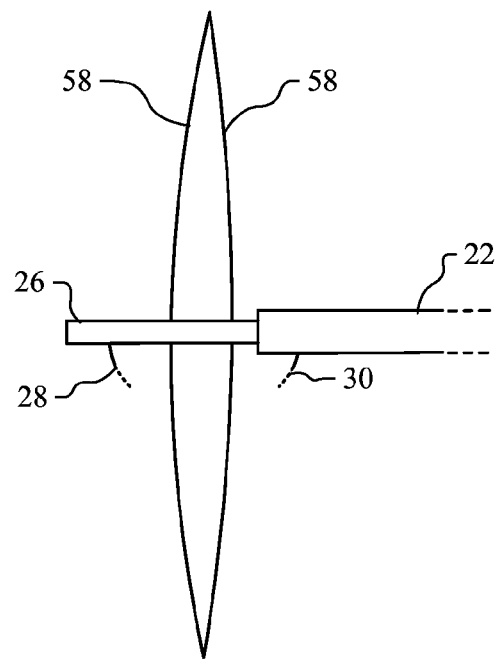
FIG. 13 is a diagrammatic view of an approximator device being used to approximate tissue edges.
Figure 14:
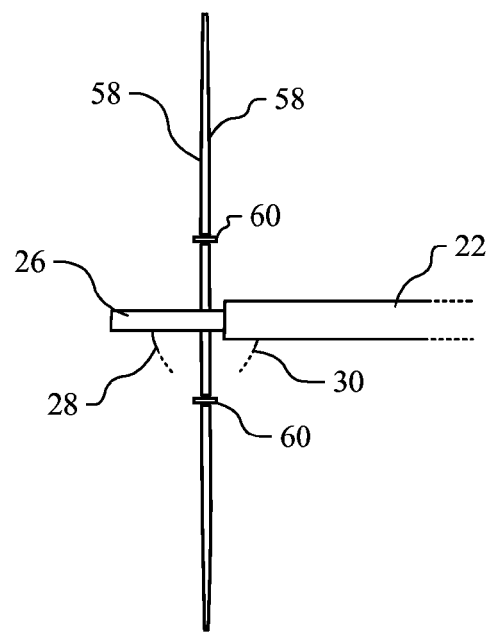
FIG. 14 is a diagrammatic view of an approximator device being used to hold tissue edges together during installation of fasteners.
Figure 15:
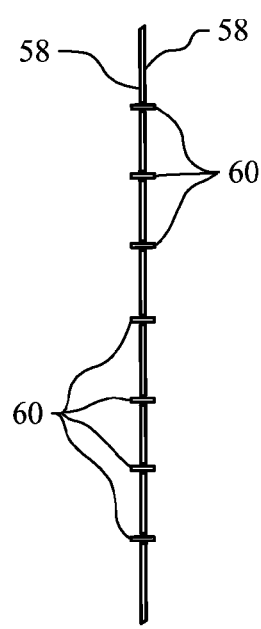
FIG. 15 is a diagrammatic view of tissue edges being fixated with fasteners.
Figure 16:
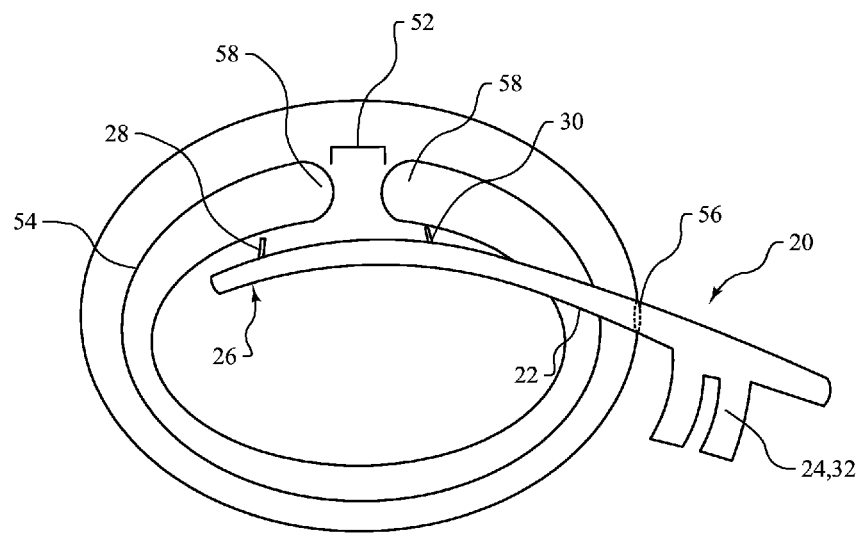
FIG. 16 is a cross-sectional diagrammatic view of abdominal tissue edges being approximated using an approximator device having an elongate member and a working end that is at least partially curved.
Figure 17:
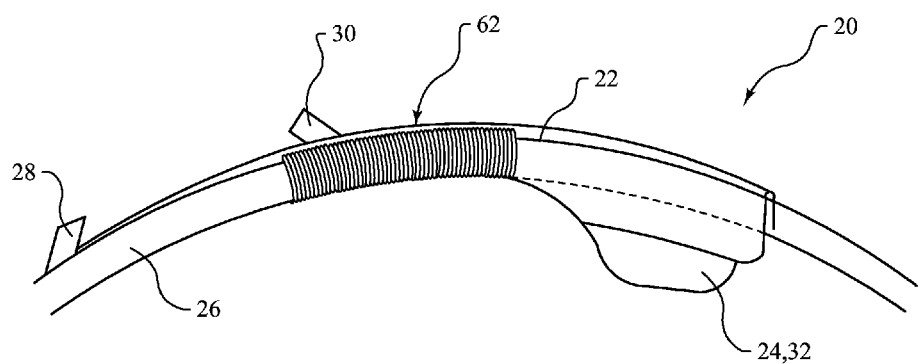
FIG. 17 is a diagrammatic view of an approximator device having an elongate member and a working end that is provided with a flexible spring-type tube.

Once the distal and proximal prongs 28, 30 engage with the corresponding tissue edges 58, the approximator device 20 may be controlled to longitudinally move the distal and proximal prongs 28, 30 toward one another as illustrated in FIG. 13 and into the fully approximated position as illustrated in FIG. 14. More specifically, while the distal and proximal prongs 28, 30 hold the respective tissue edges 58 together, fasteners 60, such as staples, sutures, or the like, may be applied to locations along the opening 52 and closest to the working end 26 of the approximator device 20, such as immediately above and immediately below the working end 26, to fixate the tissue edges 58 together as shown. The process may be repeated along the length of the opening 52 until the tissue edges 58 are sufficiently fixated together as shown for example in FIG. 15. Although the embodiments of FIGS. 10-15 employ one type of approximator device 20, it will be understood that other variations of the approximator device 20 may be similarly used to achieve the same or similar results. Among other variations, the approximator device 20, as shown in FIGS. 16 and 17 for example, may be provided with a working end 26 and/or elongate member 22 that is at least partially curved and/or flexible via a spring-type tube 62, or the like, to better conform to the inner surface of the abdominal wall 54.

Figure 18:
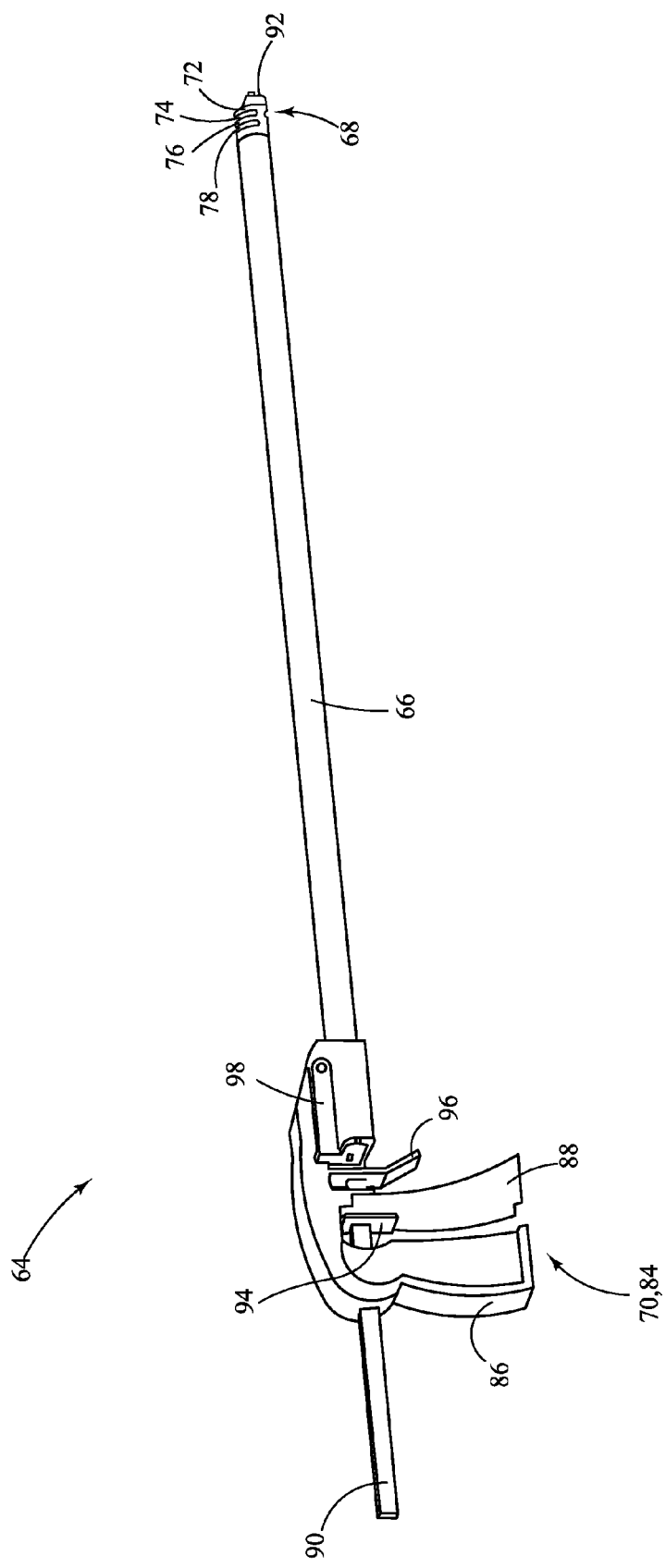
FIG. 18 is a perspective view of another approximator device constructed in accordance with the teachings of the present disclosure.

Turning now to FIG. 18, another tissue approximator device 64 that may be inserted into and beneath an abdominal wall to approximate separated edges of tissue is provided. Similar to previous embodiments, the approximator device 64 may include an elongate member 66 which extends between a working end 68 disposed at a distal end thereof and a control end 70 disposed at a proximal end thereof. The working end 68 may include a distal set of prongs, such as a first distal prong 72 and a second distal prong 74, configured to interface with a proximal set of prongs, such as a first proximal prong 76 and a second proximal prong 78. Moreover, the distal prongs 72, 74 may be longitudinally movable relative to the proximal prongs 76, 78 between an open position, as shown for example in FIG. 19, and an approximating position, as shown for example in FIG. 20. While the proximal prongs 76, 78 may be stationary and the distal prongs 72, 74 may be slidably movable relative thereto, in alternative embodiments, any combination of the distal prongs 72, 74 and the proximal prongs 76, 78 may be movable between the open and approximating positions.

Figure 19:
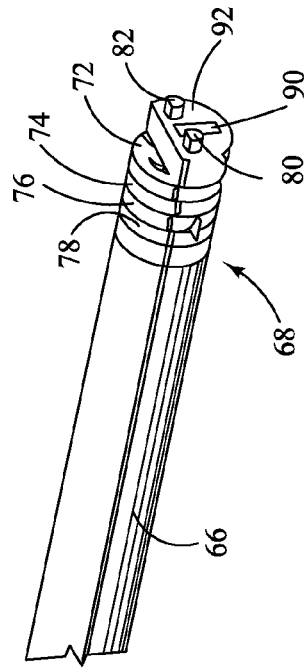
FIG. 19 is a partial perspective view of the working end of an approximator device with collapsed distal and proximal sets of prongs in the open position.
Figure 20:
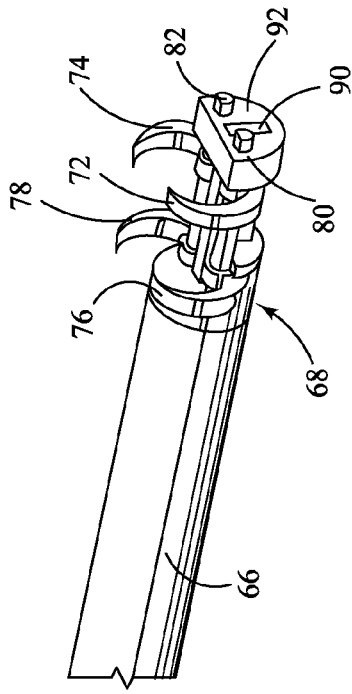
FIG. 20 is a partial perspective view of the working end of an approximator device with collapsed distal and proximal sets of prongs in the approximating position.
Figure 21:
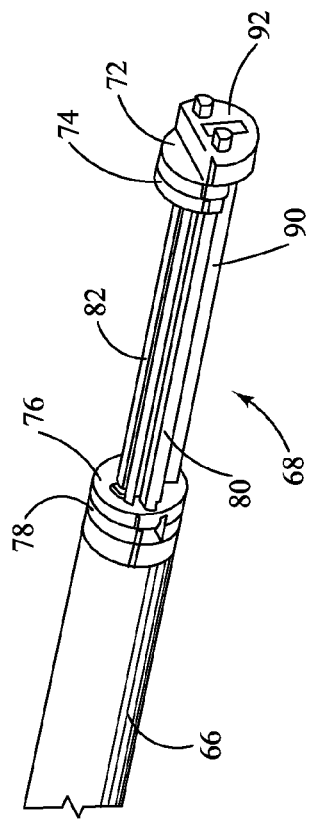
FIG. 21 is a partial perspective view of the working end of an approximator device with extended distal and proximal sets of prongs in the open position.
Figure 22:
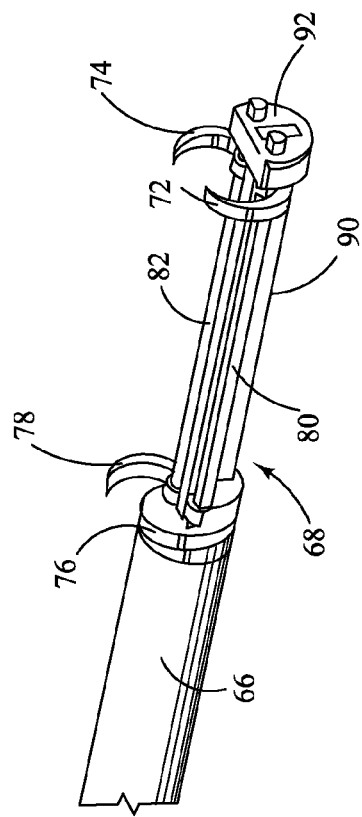
FIG. 22 is a partial perspective view of the working end of an approximator device with extended distal and proximal sets of prongs in the approximating position.

Additionally, each of the distal set of prongs 72, 74 and the proximal set of prongs 76, 78 may be pivotally movable between fully collapsed positions, as shown for example in FIGS. 19-20, and opened or extended positions, as shown for example in FIGS. 21-22. Furthermore, the distal prongs 72, 74 and the proximal prongs 76, 78 may be configured such that, when in the fully collapsed position, the maximum outer diameter of the working end 68 is less than or at most substantially equal to the maximum outer diameter of the elongate member 66 so as to facilitate insertion of the working end 68 into the abdominal wall and access ports, as well as to facilitate removal therefrom. In other modifications, the working end 68 may be configured to be at least partially retractable within the distal end of the elongate member 66 or a sleeve thereof. In other variations, one or more of the distal prongs 72, 74 and the proximal prongs 76, 78 may be biased so as to automatically pivot into the extended position once the working end 68 is advanced into a region of interest, but otherwise maintained in the collapsed state, such as while retracted within the elongate member 66, an access port, or the like.

As shown in FIGS. 19-22, the first and second distal prongs 72, 74 may be opposedly configured to receive and hold an edge of tissue therebetween, while the first and second proximal prongs 76, 78 may be opposedly configured to receive and hold a counterpart edge of tissue therebetween. In addition, the first distal prong 72 and the first proximal prong 76 may be configured to simultaneously pivot about a first deployment shaft 80 between collapsed and extended positions, while the second distal prong 74 and the second proximal prong 78 may be configured to simultaneously pivot about a second deployment shaft 82, where each of the first and second deployment shafts 80, 82 may be parallel to one another and substantially parallel to a longitudinal axis of the elongate member 66. Furthermore, the first and second deployment shafts 80, 82 may be configured to opposedly rotate in substantial synchronization with one another. Alternatively, the first and second deployment shafts 80, 82 may be controlled independently of one another. In other variations, the distal prongs 72, 74 may be controlled independently from the proximal prongs 76, 78. In other modifications, the one or more of the distal prongs 72, 74 and the proximal prongs 76, 78 may be coaxially disposed or pivotally disposed about one or more axes which may or may not be parallel with the one another and/or with the longitudinal axis of the elongate member 66. In still further modifications, the working end 68 may include fewer or more prongs than shown.

The control end 70 of the approximator device 64 of FIG. 18 may include a control mechanism 84 having, for example, a ratcheting mechanism for controlling the longitudinal movements of the prongs 72, 74, 76, 78, which is integrated with a lever-based deployment mechanism for deploying the prongs 72, 74, 76, 78. As shown in FIGS. 23-24, the control mechanism 84 may generally include a handle 86 and a trigger 88 hingably coupled thereto. The control mechanism 84 may further employ a tension bar 90 which proximally extends from a brace 92 on the working end 68 through each of the elongate member 66, the trigger 88 and the handle 86. Moreover, the tension bar 90 may be slidably configured to longitudinally shift the distal prongs 72, 74 relative to the proximal prongs 76, 78 between open and approximating positions. Movement of the tension bar 90 may be limited by one or more of a ratcheting plate 94 proximally disposed relative to the trigger 88, and a release plate 96 distally disposed relative to the trigger 88. Specifically, the ratcheting plate 94 may be configured to incrementally retract the tension bar 90 per actuation of the trigger 88, and thereby incrementally approximate the prongs 72, 74, 76, 78. The release plate 96 may be coupled to the handle 86 and configured such that, when in the default state, retraction of the tension bar 90 is limited, and when in the depressed state, manual adjustment of the tension bar 90 is enabled.

As shown in FIGS. 23-24, the control mechanism 84 may include a deployment lever 98 that is hingably coupled to the handle 86 and operatively coupled to one or more of the first and second deployment shafts 80, 82 via one or more keyed sleeves 100. In particular, the keyed sleeves 100 may be longitudinally and rotatably disposed within the elongate member 66, and configured to mateably receive keyed end portions 102 of the deployment shafts 80, 82. Moreover, the deployment lever 98 may be configured such that pivotally moving the deployment lever 98 relative to the handle 86 causes corresponding rotations in the attached keyed sleeves 100, which further causes corresponding rotations in the attached deployment shafts 80, 82 and prongs 72, 74, 76, 78. For example, pivotally advancing the deployment lever 98 in the distal direction may simultaneously move the prongs 72, 74, 76, 78 into the extended position, while pivotally retracting the deployment lever 98 may simultaneously collapse the prongs 72, 74, 76, 78.

Similar or comparable results can be achieved using any one or more of a variety of other mechanisms not shown. For example, while the embodiments shown depict the distal prongs 72, 74 to be movable relative to the proximal prongs 76, 78, the ratcheting mechanism of the control end 70 may additionally or alternatively enable longitudinal adjustment of the proximal prongs 76, 78. Rather than a ratcheting mechanism, the control end 70 may also employ any one or more of a geared mechanism, a threaded mechanism, a spring-type mechanism, a motorized mechanism, and the like. Deployment of the prongs 72, 74, 76, 78 may also be enabled by any one or more of a variety of different mechanisms. For example, the deployment lever 98 may be coupled to two keyed sleeves 100, where each keyed sleeve 100 is operatively coupled to a corresponding one of the first and second deployment shafts 80, 82. Alternatively, the deployment lever 98 may be coupled to one keyed sleeve 100 for operating one of the deployment shafts 80, 82, while the remaining deployment shaft 80, 82 is simultaneously and oppositely rotated via a geared mechanism, or the like. In still further alternatives, multiple keyed sleeves 100 may be provided, and each keyed sleeve 100 may be engaged by independently controllable deployment levers 98, or the like.

Figure 25:
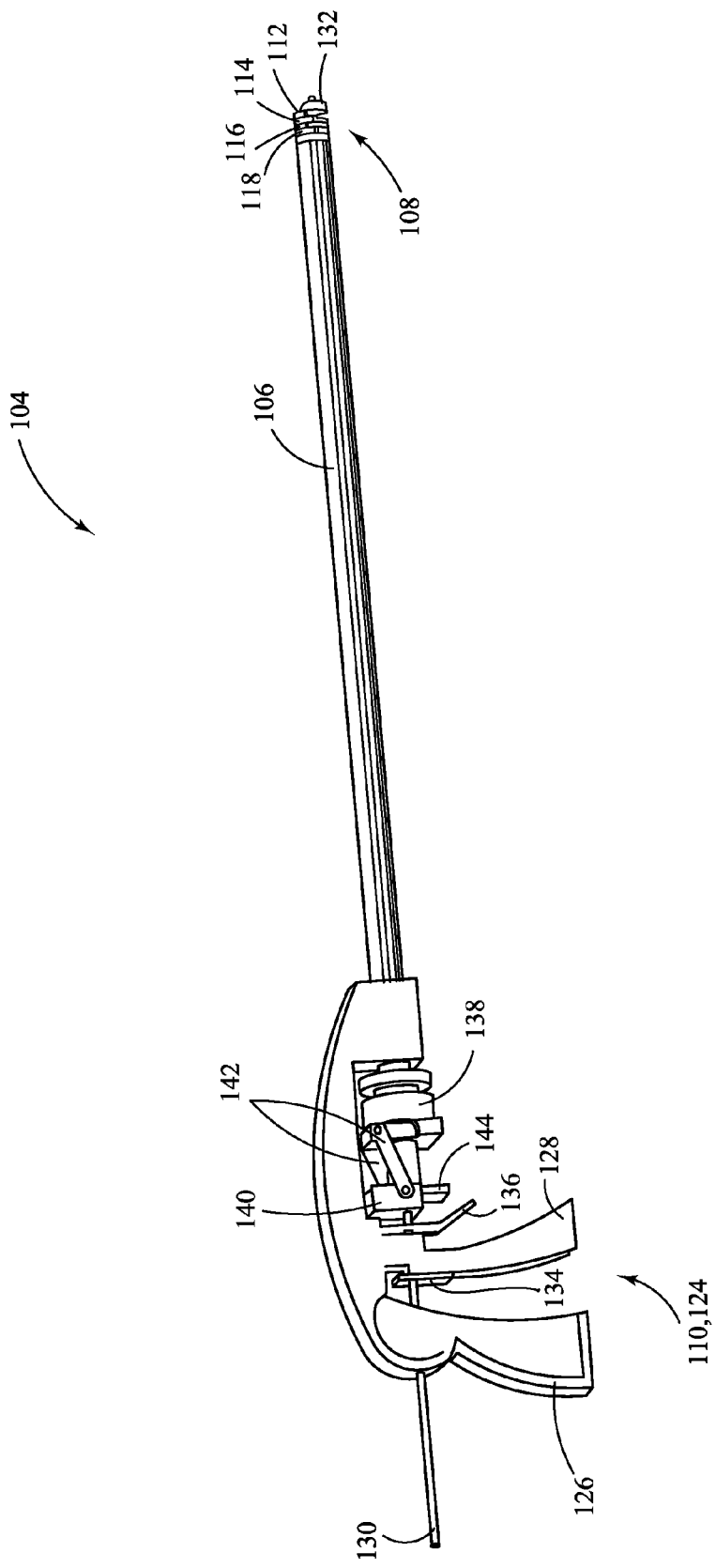
FIG. 25 is a perspective view of another approximator device constructed in accordance with the teachings of the present disclosure.
Figure 26:
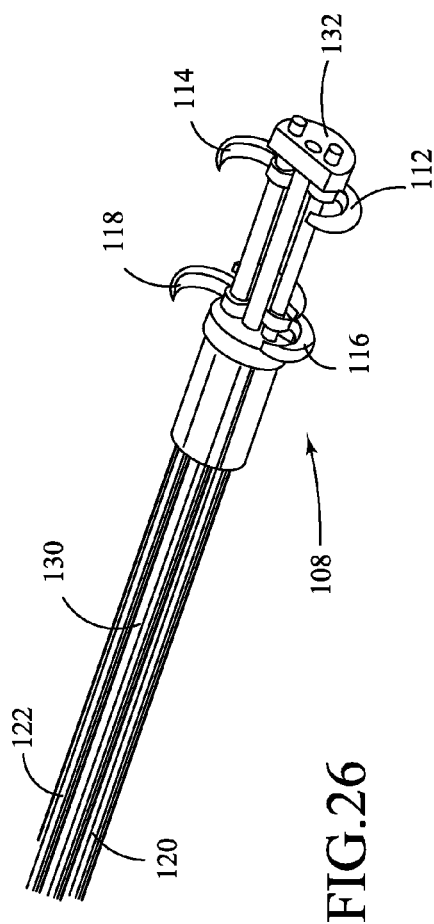
FIG. 26 is a partial perspective view of the working end of an approximator device having distal and proximal sets of prongs coupled to a rounded tension bar and deployment shafts.
Figure 27:
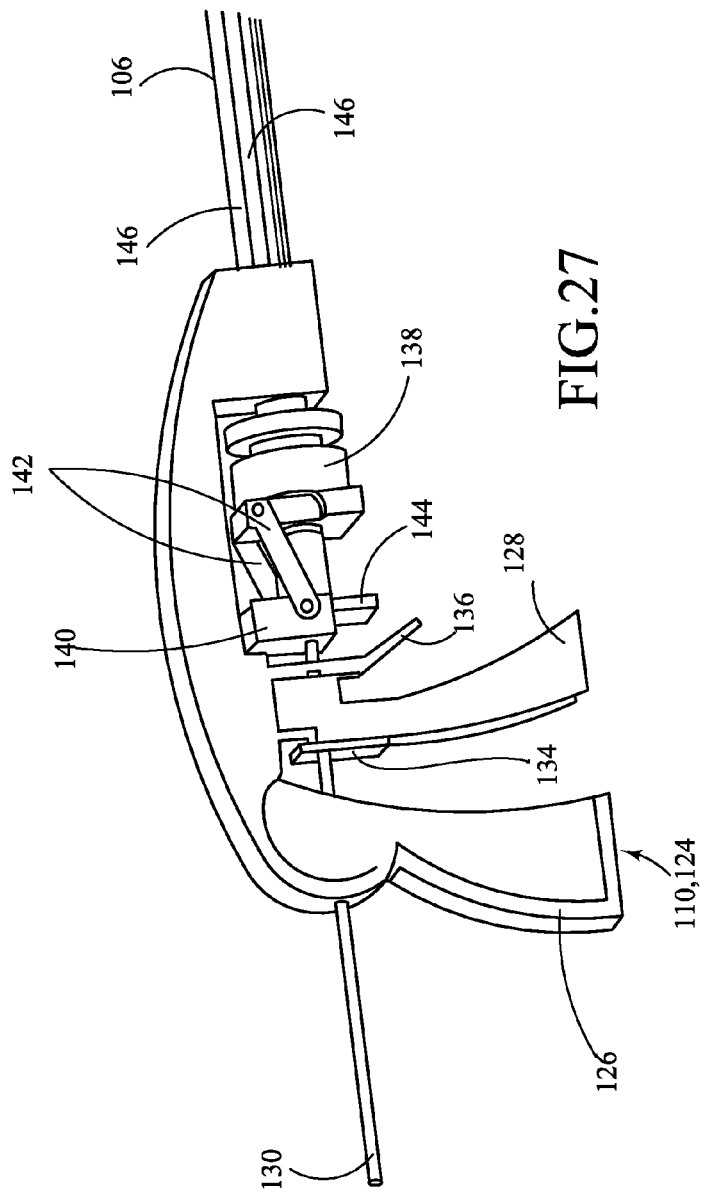
FIG. 27 is a partial perspective view of the control end of an approximator device having ratcheting and roticulating deployment control mechanisms.
Figure 28:
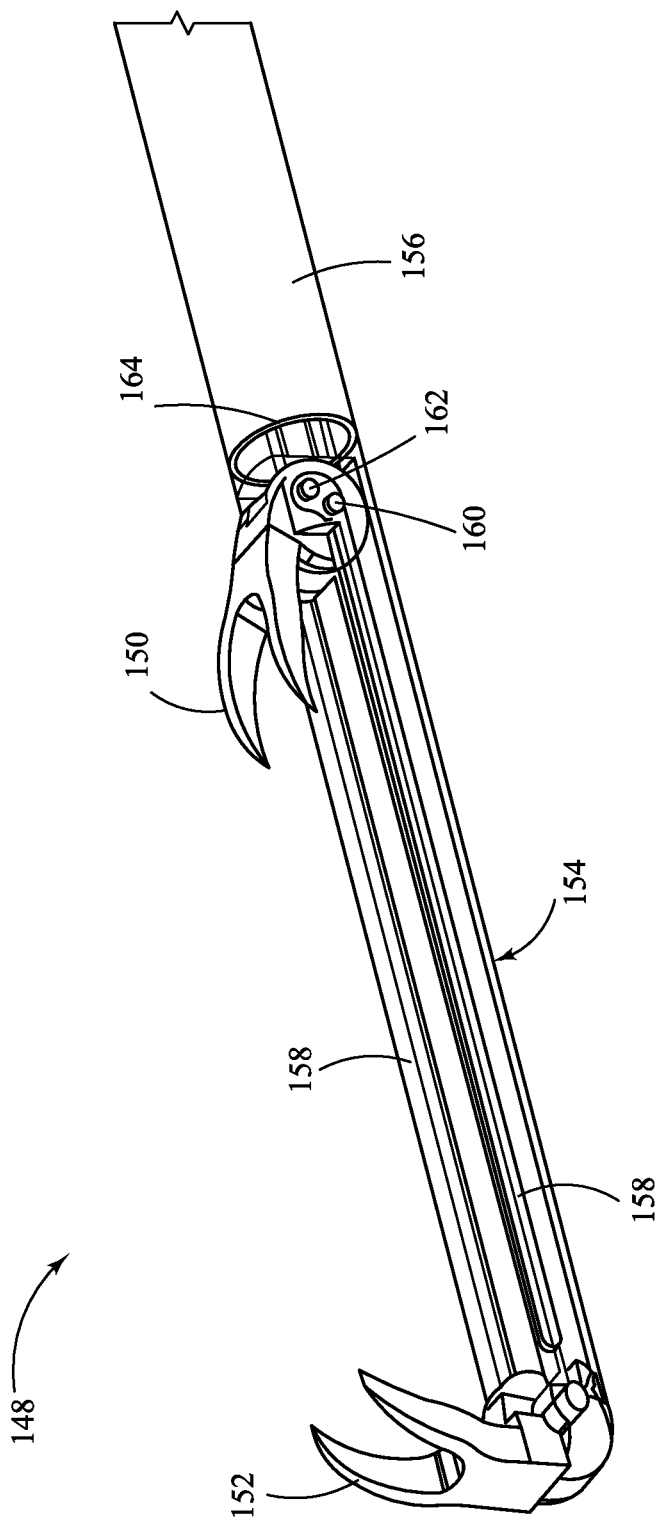
FIG. 28 is a partial perspective view of the working end of yet another approximator device constructed in accordance with the teachings of the present disclosure.

As shown in FIGS. 25-27, yet another tissue approximator device 104 that may be used to approximate separated edges of tissue is provided. As in previous embodiments, the approximator device 104 may include an elongate member 106 extending between a working end 108 disposed at a distal end thereof and a control end 110 disposed at a proximal end thereof. Similar to the working end 68 of FIG. 24, the working end 108 in FIG. 26 may include a distal set of prongs, such as a first distal prong 112 and a second distal prong 114, which interfaces with a proximal set of prongs, such as a first proximal prong 116 and a second proximal prong 118. Furthermore, the proximal prongs 116, 118 may remain stationary relative to the working end 68, while the distal prongs 112, 114 may be longitudinally movable relative to the proximal prongs 116, 118 between open and approximating positions. In alternative modifications, however, the distal prongs 112, 114 may remain stationary while the proximal prongs 116, 118 may be movable relative to the distal prongs 112, 114. In still further alternatives, both of the distal set of prongs 112, 114 and the proximal set of prongs 116, 118 may be movable relative to one another.

Each of the distal set of prongs 112, 114 and the proximal set of prongs 116, 118 shown in FIG. 26 may also be pivotally movable between fully collapsed positions and opened or extended positions. Furthermore, the distal prongs 112, 114 and the proximal prongs 116, 118 may be configured such that, when in the fully collapsed position, the maximum outer diameter of the working end 108 is less than or at most substantially equal to the maximum outer diameter of the elongate member 106 so as to facilitate insertion of the working end 108 into the abdominal wall and access ports, as well as to facilitate removal therefrom. In other modifications, the working end 108 may be configured to be at least partially retractable within the distal end of the elongate member 106 or a sleeve thereof. In other variations, one or more of the distal prongs 112, 114 and the proximal prongs 116, 118 may be biased so as to automatically pivot into the extended position once the working end 108 is advanced into a region of interest, but otherwise maintained the collapsed state, such as while retracted within the elongate member 106, an access port, or the like.

Similar to previous embodiments, the first and second distal prongs 112, 114 in FIG. 26 may be oppositely configured to receive and hold one edge of tissue therebetween, while the first and second proximal prongs 116, 118 may be oppositely configured to receive and hold a counterpart edge of tissue therebetween. In addition, the first distal prong 112 and the first proximal prong 116 may be configured to simultaneously pivot about a first deployment shaft 120, while the second distal prong 114 and the second proximal prong 118 may be configured to simultaneously pivot about a second deployment shaft 122. Furthermore, while the first and second deployment shafts 120, 122 may be configured to rotate in substantial synchronization with one another, the first and second deployment shafts 120, 122 may also be controlled independently of one another. In other variations, the distal prongs 112, 114 may be controlled independently from the proximal prongs 116, 118. In other modifications, one or more of the distal prongs 112, 114 and the proximal prongs 116, 118 may be coaxially disposed or pivotally disposed about one or more axes which may or may not be parallel with the one another or with the longitudinal axis of the elongate member 106. In still further modifications, the working end 108 may include fewer or more prongs than shown.

The control end 110 of the approximator device 104 of FIG. 27 may include a control mechanism 124 which integrates a ratcheting mechanism for controlling the longitudinal movements of the prongs 112, 114, 116, 118, with a roticulating deployment mechanism for deploying the prongs 112, 114, 116, 118. As in previous embodiments, the control mechanism 124 may generally include a handle 126 and a trigger 128 hingably coupled thereto. The control mechanism 124 may further employ a tension bar 130 which proximally extends from a brace 132 on the working end 108 through each of the elongate member 106, the trigger 128 and the handle 126. The tension bar 130 may be slidably configured to shift the distal prongs 112, 114 relative to the proximal prongs 116, 118 between open and approximating positions. The tension bar 130 may also be rounded so as to enable roticulation. By enabling roticulation, for example, the control end 110 may be rotatable relative to the elongate member 106 and the working end 108, while maintaining full control of the prongs 112, 114, 116, 118. Furthermore, because the working end 108 is engagable irrespective of the rotational position of the control end 110 relative thereto, the handle 126 and the trigger 128 may be comfortably gripped and used at any desired position. Movement of the tension bar 130 may be limited by one or more of a ratcheting plate 134 proximally disposed relative to the trigger 128, and a release plate 136 distally disposed relative to the trigger 88. The ratcheting plate 134 may be configured to incrementally retract the tension bar 130 per actuation of the trigger 128, and thereby incrementally approximate the prongs 112, 114, 116, 118. The release plate 136 may be configured such that, when in the default state, advancement of the tension bar 130 is limited, and when in the depressed state, manual adjustment of the tension bar 130 is enabled.

As shown in FIG. 27, the control mechanism 124 may be roticulating, such as provided with a deployment mechanism that is rotatable about the tension bar 130 and actuatable in any rotational orientation. For example, the deployment control mechanism 124 may include a deployment actuator 138 that is rotatably and slidably disposed about the tension bar 130 and hingably coupled to a slider cam 140 via links 142. More specifically, the slider cam 140 may be coupled to an endcap 144 such that the slider cam 140 is longitudinally fixed relative to the tension bar 130 but laterally slidable, such as within the plane defined by the endcap 144 and normal to the tension bar 130. The slider cam 140 may further be operatively coupled to one or more of the first and second deployment shafts 120, 122 via one or more keyed sleeves 146. Similar to previous embodiments, each keyed sleeve 146 may be longitudinally disposed within the elongate member 106, and configured to rotatably interface with a corresponding deployment shaft 120, 122. Furthermore, the deployment control mechanism 124 may be configured such that the prongs 112, 114, 116, 118 can be extended or collapsed from any rotational orientation relative to the handle 126.

In general, the control mechanism 124 may be configured such that shifting the deployment actuator 138 in the longitudinal direction relative to the tension bar 130 and the handle 126 laterally shifts the slider cam 140 in a manner which rotates one or more of the keyed sleeves 146, and in turn, rotates the corresponding deployment shafts 120, 122 and prongs 112, 114, 116, 118. For example, pulling the deployment actuator 138 in the proximal direction may cause the slider cam 140 to slide in the radially inward direction relative to the endcap 144, which may turn the proximal end of the keyed sleeves 146 and rotate the deployment shafts 120, 122 in a manner which extends the associated prongs 112, 114, 116, 118. Correspondingly, advancing the deployment actuator 138 in the distal direction may cause the slider cam 140 to slide in the radially outward direction relative to the endcap 144, which may turn the proximal end of the keyed sleeves 146 and rotates the deployment shafts 120, 122 in a manner which collapses the associated prongs 112, 114, 116, 118.

The roticulating deployment control mechanism 124 may alternatively be configured in any number of different ways to provide similar or comparable results. Rather than a ratcheting mechanism, for example, the control end 110 may employ any one or more of a geared mechanism, a threaded mechanism, a spring-type mechanism, a motorized mechanism, and the like, to adjust the longitudinal positions of the distal prongs 112, 114 relative to the proximal prongs 116, 118. Also, while the embodiments shown depict the distal prongs 112, 114 to be movable relative to the proximal prongs 116, 118, other variations may additionally or alternatively enable longitudinal adjustment of the proximal prongs 116, 118. Deployment of the prongs 112, 114, 116, 118 may also be enabled by any one or more of a variety of different mechanisms. For example, the slider cam 140 may be coupled to two keyed sleeves 146, where each keyed sleeve 146 is operatively coupled to a corresponding one of the first and second deployment shafts 120, 122. Alternatively, the slider cam 140 may be coupled to one keyed sleeve 146 for operating one of the deployment shafts 120, 122, while the remaining deployment shaft 120, 122 is simultaneously and oppositely rotated via a geared mechanism, or the like.

Referring now to FIGS. 28-32, yet another embodiment of an approximator device 148 is provided. The approximator device 148 shown in FIGS. 28-32 may follow the general form factor of the approximator device 20 of FIGS. 1-8, for example, having proximal and distal prongs 150, 152 disposed at a working end 154 of an elongate member 156 that are operated to longitudinally interface with one another via a pushrod-type or comparable control mechanism. In contrast to the embodiments of FIGS. 1-8, each of the proximal and distal prongs 150, 152 may have a claw-shaped configuration rather than a tong-shaped configuration, and the deployment screw 40 and deployment link 44 may be replaced with one or more cam slots 158 and camming pins 160, 162 as shown. More specifically, the proximal prong 150 may be movably coupled to a pushrod 164, either directly or indirectly via a tension bar, or the like, and configured to pivot about the first pin 160. Furthermore, each of the first pin 160 and the second pin 162 may be sized and configured to be movably received within the cam slots 158 such that moving the pins 160, 162 along the cam slots 158 effectuate a camming motion in the proximal prong 150, as shown for example in FIGS. 29-32.

Figure 29:
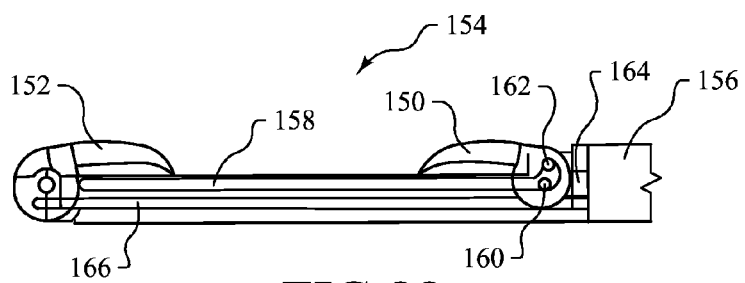
FIG. 29 is a partial side view of the working end of an approximator device having a collapsed distal prong and a collapsed and cammed proximal prong in the open position.
Figure 30:
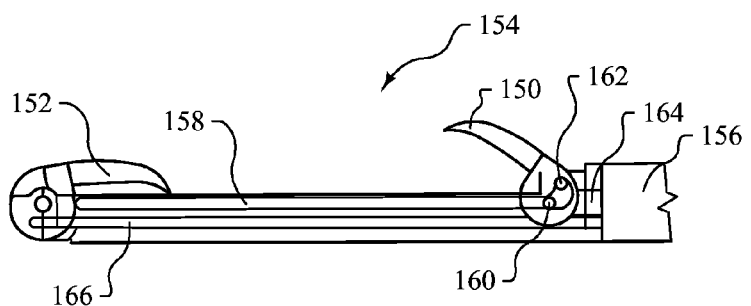
FIG. 30 is a partial side view of the working end of an approximator device having a collapsed distal prong and a partially extended and cammed proximal prong in the open position.
Figure 31:
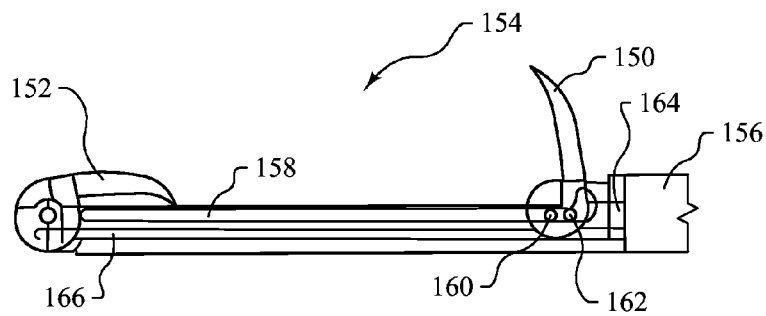
FIG. 31 is a partial side view of the working end of an approximator device having a collapsed distal prong and an extended and cammed proximal prong in the open position.
Figure 32:
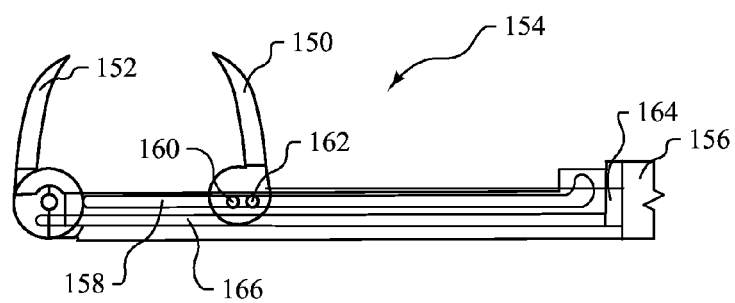
FIG. 32 is a partial side view of the working end of an approximator device having an extended distal prong and an extended and cammed proximal prong in a partially approximating position.

As the proximal prong 150 is retracted and proximally moved into the open position shown for example in FIG. 29, such as by pulling the pushrod 164, the edges of the cam slots 158 may cause the pins 160, 162 to cam or rotate the proximal prong 150 into the collapsed position shown. Correspondingly, as the proximal prong 150 is distally moved toward the approximating position, such as by pushing the pushrod 164, the edges of the cam slots 158 may guide the pins 160, 162 in a manner which cams or rotates the proximal prong 150 into the extended position, as progressively shown in FIGS. 30-31. As shown in FIG. 32, the distal prong 152 may be movable between collapsed and extended positions using a deployment link 166 and means similar to those shown in FIGS. 1-8, or any other comparable deployment mechanism. In such a way, the approximator device 148 of FIGS. 28-32 is able to automatically extend when approximation is desired and automatically collapse when approximation is not needed. In other alternative modifications, a single cam slot may be provided and configured to interact with one end of each camming pin. In other modifications, more than two cam slots may be provided to interact with a plurality of camming pins. In still further alternatives, a single camming pin may be provided with one or more ends having oblique, oval, elliptical, or any other suitable cross-sections which enable camming motions.

From the foregoing, it can be seen that the present disclosure sets forth a medical approximator device adapted to efficiently and effectively approximate tissue during minimally invasive surgical procedures. Through the improved ease of use and the reduction in time required for fastening tissue separations, the approximator device facilitates more reliable and efficient achievement of tissue fixation.

What is claimed is:
1. An approximator device, comprising:
an elongate member having a working end and a control end;
at least two prongs disposed on the working end configured to engage tissue and longitudinally interface with one another, each of the at least two prongs movable relative to the elongate member between an extended position and a collapsed position; and
a control mechanism disposed at the control end operatively coupled to one or more of the prongs and configured to longitudinally move the one or more prongs between an open position and an approximating position, and configured to cause one or more of the prongs to pivotally move between the extend position and the collapsed position.

2. The approximator device of claim 1, wherein the elongate member is at least partially curved.

3. The approximator device of claim 1, wherein the elongate member is at least partially flexible.

4. The approximator device of claim 1, wherein the prongs are configured such that, in the collapsed position, a maximum outer diameter of the working end does not exceed an outer diameter of the elongate member, and in the extended position, enable sufficient approximation of tissue.

5. The approximator device of claim 1, wherein the prongs are configured such that, in the collapsed position, the prongs and the working end are at least partially retractable within the elongate member.

6. The approximator device of claim 1, wherein each of the prongs is movable about an axis substantially perpendicular to a longitudinal axis of the elongate member.

7. The approximator device of claim 1, wherein each of the prongs is movable about an axis substantially parallel to a longitudinal axis of the elongate member.

8. The approximator device of claim 1, wherein the prongs include a proximally-facing distal prong and a distally-facing proximal prong, at least one of the proximal prong and the distal prong being longitudinally movable relative to the elongate member.

9. The approximator device of claim 1, wherein the control mechanism employs one of a ratcheting mechanism and a pushrod mechanism to move one or more of the prongs into the approximating position.

10. The approximator device of claim 1, wherein the control mechanism employs one or more of a camming mechanism, a lever mechanism, a screw mechanism, and a switch mechanism to move one or more of the prongs into one or more of an extended position and a collapsed position.

11. The approximator device of claim 1, wherein one or more of the prongs are pivotally biased relative to the working end so as to automatically move into one or more of an extended position and a collapsed position once deployed.

12. An approximator device, comprising:
an elongate member having a working end and a control end;
one or more distal prongs pivotally disposed on the working end;
one or more proximal prongs pivotally disposed on the working end; and
a control mechanism disposed at the control end and operatively coupled to one or more of the distal prongs and the proximal prongs, the control mechanism being configured to cause one or more of the distal prongs and the proximal prongs to longitudinally move between an open position and an approximating position, and pivotally move between an extended position and a collapsed position.

13. The approximator device of claim 12, wherein the elongate member is at least partially configured to conform to a curve.

14. The approximator device of claim 12, wherein the distal prongs include at least a first distal prong and a second distal prong configured to pivotally interface with one another, and the proximal prongs include at least a first proximal prong and a second proximal prong configured to pivotally interface with one another.

15. The approximator device of claim 12, wherein the elongate member includes a tension bar, a first deployment shaft and a second deployment shaft longitudinally disposed therein operatively coupling the distal prongs and the proximal prongs to the control mechanism, the control mechanism engaging the tension bar to cause one or more of the distal prongs and the proximal prongs to longitudinally move between an open position and an approximating position, engaging the first deployment shaft to rotate each of the first distal prong and the first proximal prong, and engaging the second deployment shaft to rotate each of the second distal prong and the second proximal prong.

16. The approximator device of claim 12, wherein the distal prongs and the proximal prongs are configured such that, in the collapsed position, a maximum outer diameter of the working end does not exceed an outer diameter of the elongate member.

17. An approximator device, comprising:
an elongate member having a working end and a control end, the working end including a distal prong set and a proximal prong set;
a deployment mechanism disposed at the control end and operatively coupled to each of the distal prong set and the proximal prong set, the deployment mechanism being configured to pivotally move one or more of the distal prong set and the proximal prong set between an extended position and a collapsed position; and
an approximating mechanism disposed at the control end and operatively coupled to one or more of the distal prong set and the proximal prong set, the approximating mechanism being configured to longitudinally move one or more of the distal prong set and the proximal prong set between an open position and an approximating position.

18. The approximator device of claim 17, wherein the distal prong set includes a first distal prong that is pivotally opposed to a second distal prong, and the proximal prong set includes a first proximal prong that is pivotally opposed to a second proximal prong, each of the individual prongs being independently movable.

19. The approximator device of claim 17, wherein the deployment mechanism includes one or more deployment shafts operatively coupled to one or more of the distal prong set and the proximal prong set, and the approximating mechanism employs one of a ratcheting mechanism and a pushrod mechanism operatively coupled to one or more of the distal prong set and the proximal prong set.

20. The approximator device of claim 17, wherein the elongate member is at least partially configured to conform to a curve, and one or more of the deployment mechanism and the approximating mechanism is operatively coupled to a handle disposed on the control end of the elongate member.

21. The approximator device of claim 17, further comprising a roticulating mechanism rotatably coupling the working end to the control end, the roticulating mechanism operatively interfacing the distal prong set and the proximal prong set with the deployment mechanism.

* * * * *